United States Patent [19]
Gala

[11] Patent Number: 5,545,558
[45] Date of Patent: Aug. 13, 1996

[54] SELECTION OF CHIRAL α-HYDROXYKETONES AND DERIVATIVES USING LIPASE

[75] Inventor: Dinesh Gala, East Brunswick, N.J.

[73] Assignee: Schering Corporation, Kenilworth, N.J.

[21] Appl. No.: 211,336
[22] PCT Filed: Oct. 1, 1992
[86] PCT No.: PCT/US92/08168
    § 371 Date: Mar. 29, 1994
    § 102(e) Date: Mar. 29, 1994

Related U.S. Application Data

[63] Continuation-in-part of Ser. No. 771,260, Oct. 4, 1991, abandoned.

[51] Int. Cl.$^6$ ................................................ C12P 41/00
[52] U.S. Cl. ........................ 435/280; 435/135; 435/136
[58] Field of Search ...................................... 435/280, 135, 435/136

[56] References Cited

U.S. PATENT DOCUMENTS

| | | | |
|---|---|---|---|
| 3,338,796 | 8/1967 | Rothrock | 435/148 |
| 4,929,760 | 5/1990 | Kitazume et al. | 568/308 |
| 5,026,642 | 6/1991 | Radunz et al. | 435/117 |
| 5,061,629 | 10/1991 | Coffen et al. | 435/280 |
| 5,079,153 | 1/1992 | Enomoto et al. | 435/126 |

FOREIGN PATENT DOCUMENTS 0325971 8/1989 European Pat. Off. .
62-208298 9/1987 Japan .
1-240198 9/1989 Japan .

OTHER PUBLICATIONS

Duh T. H. et al., J. Chinese Chem. Soc. 39: 465–469 (1992).
Cambou et al., Biotech Bioengin XXVI:1449–1454 (1984).
Kirchner G. et al., J. Am. Chem. Soc. 107:7072–7076 (1985).
Langrand G. et al., Tetrahedron Lett 27:29–32 (1986).
Saji et al., "The 28th Interscience Conference on Antimicrobial Agents and Chemotherapy", Los Angeles, Oct. 1988, p. 140.
Konosu et al., Chem. Pharm. Bull., 38, 8477–8482 (1988).
Davis et al., J. Amer. Chem. Soc., 110, 8477–8482 (1988).
Davis et al., J. Org. Chem., 56, 1143–1145 (1991).
Chenevert et al., Chem. Lett., 1191–1192 (1988).
Konishi et al., Chem. Lett., 1111–1112 (1985).
Matsumoto et al., Tet. Lett., 31, (49) 7163–7166 (1990).
Ohta et al., Chem. Lett., 1169–1172 (1986).
Bianchi et al., Tetrahedron, 45, (3) 869–876 (1989).
DeKimpe. et al., Chem Ber., 116, 3631–3636 (1983).
Gala et al., J. Pharmaceut. Sciences, 81, 1199–1203 (1992).

Primary Examiner—Michael G. Wityshyn
Assistant Examiner—Sandra Saucier
Attorney, Agent, or Firm—Paul A. Thompson

[57] ABSTRACT

A process for the preparation of a chiral α-hydroxylketone, or ester thereof, comprising hydrolyzing an ester of said α-hydroxyketone with an enzyme that has a specificity for one enantiomer, or by esterifying said α-hydroxyketone with an esterifying agent in the presence of an enzyme that favors one enantiomer.

12 Claims, No Drawings

SELECTION OF CHIRAL α-HYDROXYKETONES AND DERIVATIVES USING LIPASE

The present application is the United States national application corresponding to International Application No. PCT/US92/08168, filed Oct. 1, 1992 and designating the United States, which PCT application is in turn a continuation-in-part of U.S. application Ser. No. 07/771,260, filed Oct. 4, 1991, now abandoned, the benefit of which are claimed pursuant to the provisions of 35 U.S.C. §120,363 and 365(C).

This invention relates to a process for preparing chiral α-hydroxyketones, and esters thereof, by hydrolyzing esters of said α-hydroxyketones with an enzyme that has a specificity for one enantiomer, or by esterifying said α-hydroxyketones with an esterifying agent in the presence of an enzyme that favors the esterification of one enantiomer, leaving the other enantiomer unchanged.

BACKGROUND

Chiral α-hydroxyketones are useful in the preparation of antimicrobials, for example: antifungals of the type described by Saji et al., "The 28th Interscience Conference on Antimicrobial Agents and Chemotherapy", Los Angeles, Oct. (1988), p. 140; and anti-fungal and anti-bacterials, such as: (+)-(2S,3S)-2-(2,4-difluoro-phenyl)-3-methylsulfonyl-1-(1,2,4-triazol-1-yl)-butan-2-ol and (−)-(2R,3R)-2-(2,4-difluorophenyl)-3-methylsulfonyl-1-(1,2,4-triazol-1-yl)-butan-2-ol, as disclosed by Konosu et al., Chem. Pharm. Bull. 1990, 38, 2476.

The preparation of chiral α-hydroxyketones and their derivatives by chemical methods is described in co-owned, co-pending U.S. application Ser. No. 07/676,042, filed Mar. 27, 1991. It is mainly by chemical methods that the literature teaches the synthesis of chiral α-hydroxyketones, e.g: Davis et al., J. Org. Chem., 1991, Vol. 56, pp 1143–1145; and Davis et al., J. Am. Chem. Soc., 1988, Vol. 110, pp. 8477–8482. However, Chenecert et al., Chemistry Letters, 1988, pp. 1191–1192, and Konishi et al., Chemistry Letters, 1985, pp. 1111–1112, show microbial synthesis of chiral α-hydroxyketones by reduction of diketones; and Matsumoto et al., Tetrahedron Lett. 1990, pp. 7163–7166, shows the enzymatic synthesis of chiral α-hydroxyketones by hydrolysis of enol esters.

Bianchi et al., Tetrahedron, 1989, Vol. 45, pp. 869–876, have shown that α-hydroxy aldehydes can be prepared by enzymatic hydrolysis of corresponding esters using lipases, such as from Pseudomonas species. However, the results obtained using aldehydes cannot be extrapolated to α-hydroxy ketones due to the greater steric effects inherent in the latter.

The asymmetric hydrolysis of α-acetoxyacylphenones by enzyme-mediated hydrolysis using a whole organism is disclosed by Ohta et al., Chem Letters, 1986, pp. 1169–1172 and by Yuki Gosei Yankuhin, in Japanese Patent Publication No. J6-2208298. Problems with the use of a whole organism include: low yields and/or slow reaction rates due to poor transport of the substrate or product across the cell membrane; poisoning of the organism by the substrate or the product; difficulties isolating the desired product from other products; and low yields due metabolism of the substrate or product through the action of other enzymes.

SUMMARY OF THE INVENTION

The present invention provides a process for the preparation of a chiral α-hydroxyketone or an ester of a chiral α-hydroxyketone, comprising: selectively hydrolyzing an ester of a racemic α-hydroxyketone with an enzyme that has a specificity for one enantiomer, or selectively esterifying a racemic α-hydroxyketone with an esterifying agent in the presence of an enzyme that favors the formation of one enantiomeric ester, optionally racemizing unchanged enantiomers and recycling the resulting racemate through the selective hydrolysis, or esterification, as described above; and isolating said chiral α-hydroxyketone or ester thereof.

Preferred is a process wherein the α-hydroxyketone, or ester thereof, is a compound of the formula

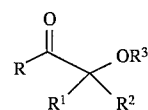

wherein:

R is selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl or substituted heteroaryl;

$R^1$ and $R^2$ must be different, and are independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl or substituted heteroaryl;

$R^3$ is H, or a carboxylic acyl group of the formula $R^4$—C(O)—;

$R^4$ is alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl or substituted heteroaryl; or R and any of $R^1$, $R^2$ or $R^4$, together with the intervening atoms to which they are attached, comprise a 5- to 10-membered carbocyclic ring or a 5- to 10-membered O, N or S containing heterocyclic ring, and wherein the carbocyclic or heterocyclic ring is optionally fused to a aryl or heteroaryl group; or $R^1$ and $R^2$, together with the carbon to which they are attached, comprise a 4- to 10- membered carbocyclic ring or a 4- to 10-membered heterocyclic ring, containing 1 to 3 O, N or S heteroatoms, wherein the carbocyclic or heterocyclic ring optionally contains one or two double bonds, provided that there is no plane of symmetry across the ring so formed; or $R^4$ and either $R^1$ or $R^2$, together with the intervening atoms to which they are attached, comprise a 4- to 10-membered heterocyclic ring, containing 0 to 2 heteroatoms selected from O, N or S, in addition to the —$OR^3$ oxygen atom, wherein the heterocyclic ring optionally contains 1 or 2 double bonds.

More preferred is a process wherein the α-hydroxyketone ester is a compound of the formula I, wherein $R^3$ is $R^4$—C(O)— and $R^4$ is lower alkyl, or substituted lower alkyl.

Another more preferred process is that wherein the α-hydroxyketone, or ester thereof, is a compound of the formula I wherein: R is alkyl, substituted alkyl, aryl or substituted alkyl, heteroaryl or substituted heteroaryl; and $R^1$ and $R^2$ are different, and independently selected from hydrogen, alkyl, substituted alkyl, aryl or substituted alkyl.

Especially preferred is a process wherein the α-hydroxyketone ester is a compound of the formula I, wherein $R^3$ is $R^4$—C(O)— and $R^4$—C(O)— is acetyl, propionyl, butyryl, malonyl, oxalyl, gluconyl, succinoyl or chloroacetyl.

Most preferred is a process wherein the the hydrolysis of the α-hydroxyketone ester is carried out in aqueous solution, an aqueous solution in the presence of a water-miscible organic solvent, or an aqueous solution in the presence of a water-immiscible organic solvent and either a solubilizing agent that improves the miscibility of the phases or a chemical that encourages phase transfer of the substrate, product or enzyme The present process offers advantages over the prior art in that either the α-hydroxyketone or its ester, whichever is desired, can be obtained in up to 99% optical purity and in yields of about 50%.

DETAILED DESCRIPTION OF THE INVENTION

The chiral α-hydroxyketone or ester thereof will have an asymmetrically substituted carbon atom adjacent to the keto-carbonyl group, and this carbon atom will carry the α-hydroxy group or esterified α-hydroxy group and at most one hydrogen atom.

As used herein, the definitions of the following terms are applicable:

"alkyl" means a straight or branched chain hydrocarbon of 1 to 18 carbon atoms;

"substituted alkyl" means an alkyl group substituted by 1 to 5 substituents independently selected from the group consisting of lower alkyl, hydroxy, lower alkoxy, lower alkenoxy, cyano, nitro, carboxyl, amino, lower alkylamino, di-(lower alkyl)amino, aminocarbonyl, N-(lower alkyl)aminocarbonyl, N,N-di-(lower alkyl)aminocarbonyl, lower alkoxycarbonyl, lower alkylthio, lower alkyl—S(O)—, lower alkyl—S(O)$_2$—, lower alkanoyl, halogeno, trifluoromethyl, phenyl, phenoxy or phenylthio;

"lower alkyl" means an alkyl group of 1 to 6 carbon atoms;

"lower alkoxy" means an alkoxy group having from 1 to 6 carbon atoms;

"lower alkenoxy" means an alkoxy group having from 2 to 6 carbon atoms and 1 to 2 carbon-carbon double bonds;

"halogeno" means a fluorine, chlorine, bromine or iodine radical;

"alkenyl" means a straight or branched chain hydrocarbon of 2 to 18, preferably from 2 to 6, carbon atoms having 1 to 4 carbon-carbon double bonds;

"substituted alkenyl" means an alkenyl group substituted by 1 to 5 substituents independently selected from the group consisting of lower alkyl, hydroxy, lower alkoxy, lower alkenoxy, cyano, nitro, carboxyl, amino, lower alkylamino, di-(lower alkyl)amino, aminocarbonyl, N-(lower alkyl)aminocarbonyl, N,N-di-(lower alkyl)aminocarbonyl, lower alkoxycarbonyl, lower alkylthio, lower alkyl—S(O)—, lower alkyl—S(O)$_2$—, lower alkanoyl, halogeno, trifluoromethyl, phenyl, phenoxy or phenylthio;

"alkynyl" means a straight or branched chain hydrocarbon of 2 to 18, preferably from 2 to 6, carbon atoms having 1 to 4 carbon-carbon triple bonds;

"substituted alkynyl" means an alkynyl group substituted by 1 to 5 substituents independently selected from the group consisting of lower alkyl, hydroxy, lower alkoxy, lower alkenoxy, cyano, nitro, carboxyl, amino, lower alkylamino, di-(lower alkyl)amino, aminocarbonyl, N-(lower alkyl)aminocarbonyl, N,N-di-(lower alkyl)aminocarbonyl, lower alkoxy-carbonyl, lower alkylthio, lower alkyl—S(O)—, lower alkyl—S(O)$_2$—, lower alkanoyl, halogeno, trifluoromethyl, phenyl, phenoxy or phenylthio;

"cycloalkyl" means a saturated carbocyclic ring having from 3 to 9, preferably from 3 to 6, carbon atoms;

"substituted cycloalkyl" means a cycloalkyl group substituted by 1 to 5 substituents independently selected from the group consisting of lower alkyl, hydroxy, lower alkoxy, lower alkenoxy, cyano, nitro, carboxyl, amino, lower alkylamino, di-(lower alkyl)amino, aminocarbonyl, N-(lower alkyl)aminocarbonyl, N,N-di-(lower alkyl)aminocarbonyl, lower alkoxycarbonyl, lower alkylthio, lower alkyl—S(O)—, lower alkyl—S(O)$_2$—, lower alkanoyl, halogeno, trifluoromethyl, phenyl, phenoxy or phenylthio;

"cycloalkenyl" means a carbocyclic ring having from 3 to 9, preferably from 5 to 7, carbon atoms, containing 1 to 3 carbon-carbon double bonds";

"substituted cycloalkenyl" means a cycloalkenyl group substituted by 1 to 5 substituents independently selected from the group consisting of lower alkyl, hydroxy, lower alkoxy, lower alkenoxy, cyano, nitro, carboxyl, amino, lower alkylamino, di-(lower alkyl)amino, aminocarbonyl, N-(lower alkyl)aminocarbonyl, N,N-di-(lower alkyl)aminocarbonyl, lower alkoxy-carbonyl, lower alkylthio, lower alkyl—S(O)—, lower alkyl—S(O)$_2$—, lower alkanoyl, halogeno, trifluoromethyl, phenyl, phenoxy or phenylthio;

"aryl" means a $C_6$–$C_{12}$ carbocyclic aromatic group, such as phenyl or naphthyl;

"substituted aryl" means an aryl group substituted by 1 to 5 substituents independently selected from the group consisting of lower alkyl, hydroxy, lower alkoxy, lower alkenoxy, cyano, nitro, carboxyl, amino, lower alkylamino, di-(lower alkyl)amino, aminocarbonyl, N-(lower alkyl)aminocarbonyl, N,N-di-(lower alkyl)aminocarbonyl, lower alkoxycarbonyl, lower alkylthio, lower alkyl—S(O)—, lower alkyl—S(O)$_2$—, lower alkanoyl, halogeno, trifluoromethyl, phenyl, phenoxy or phenylthio, or wherein two substituents attached to adjacent carbons together comprise a fused 5- or 6-membered ring containing 0 or 1 heteroatoms selected from N, O and S, e.g. dihydrobenzofuranyl, dihydrobenzothienyl, or indanyl;

"heteroaryl" means an aromatic group having from 2 to 14, preferably from 2 to 9, carbon atoms and from 1 to 3 heteroatoms, selected from O, N and S, such as pyridyl, furanyl, thienyl, thiazolyl, imidazolyl, pyrimidinyl, pyrazinyl, pyridazinyl, triazinyl, thiadizolyl, benzofuranyl, indolyl, benzothienyl, pyrazolyl or oxazolyl; and "substituted heteroaryl" means a heteroaryl group substituted by 1 to 5 substituents independently selected from the group consisting of lower alkyl, hydroxy, lower alkoxy, lower alkenoxy, cyano, nitro, carboxyl, amino, lower alkylamino, di-(lower alkyl)amino, aminocarbonyl, N-(lower alkyl)aminocarbonyl, N,N-di-(lower alkyl)aminocarbonyl, lower alkoxycarbonyl, lower alkylthio, lower alkyl—S(O)—, lower alkyl—S(O)$_2$—, lower alkanoyl, halogeno, trifluoromethyl, phenyl, phenoxy or phenylthio.

One of ordinary skill in the art will recognize that the number of double bonds present in an alkenyl, alkenoxy or cycloalkenyl group will be dependent upon the number of carbon atoms in the group, i.e. longer carbon chains can include a larger number of double bonds. Similarly, the number of triple bonds occurring in an alkynyl group will also depend on the length of the alkynyl chain. Further, it will be evident to one of ordinary skill in the art that the number and nature of substitutents occurring on substituted groups will vary with the length and/or degree of branching of the chain, in the case of acyclic groups, e.g. alkyl, alkenyl, alkynyl, alkoxy or alkenoxy, or with the size and/or number of rings in the case of cyclic groups, e.g. cycloalkyl, cycloalkenyl, aryl and heteroaryl.

The enzyme of the instant process is selected from the group consisting of lipase, lipoprotein, protease, kinase (e.g. an enterokinase), esterase (e.g. a phosphoesterase), p-glucuronidase, hydrolase, transferase, lyase, ligase, or urease. The source organism for the enzyme can be any appropriate organism, examples of which include, but are not limited to, yeast, bacterial, avian, reptilian, fish, mammalian or plant. The yield and optical purity of the product obtained are dependant upon the enzyme and substrate used in the instantly claimed process. Specific examples of enzymes that have proved suitable include:

Lipase from hog pancreas, lipase type XIII from Pseudomonas sp., lipase type II from porcine pancreas, lipase AK from Pseudomonas sp., lipase PS-30 from *Pseudomonas cepacia*, lipase CES from Pseudomonas sp., lipase AP-6 from *Aspergillus niger*, lipase AP-12 from *Aspergillus niger*, lipase PS-30 from *Pseudomonas cepacia*, lipase AK from Pseudomonas sp., PLE-A-Amano from porcine liver, LPL-50S from Amano (Pseudomonas sp.), LPL-80 from Amano (Pseudomonas sp.), LPL-200S from Amano (Pseudomonas sp.), β-glucuronidase from bovine liver, enterokinase from bovine intestine, urease Type X from *Bacillus pasteurii*, and esterase type I from porcine liver.

The hydrolysis can be carried out in aqueous solution, optionally in the presence of an organic solvent, such as a lower alkyl alcohol (e.g., methanol, ethanol or 2-propanol), acetone, di-methoxyethane (DME), or di-methylsulfoxide (DMSO), which can increase the solubility of the starting material and/or the product. Separation of the ester and the α-hydroxyketone can be accomplished based upon solubility differences, e.g., by using an almost insoluble ester as starting material and obtaining a soluble α-hydroxyketone as product. The organic solvent may be water-miscible (to provide a single-phase reaction medium), or water-immiscible (to provide a two-phase liquid medium). Where a water-immiscible solvent is used: a solubilizing agent, e.g., a water-miscible solvent, can be added to improve the miscibility of the phases; or the reaction can be carried out in the presence off a phase transfer catalyst.

The enzyme can be used as such or be supported on a polymer. Where the enzyme is supported on a polymer, the hydrolysis or esterification can be carried out batch-wise or continuously. Continuous hydrolysis or esterification can be carried out by passing a solution of the α-hydroxyketone, or ester, slowly through a column containing the enzyme supported on the polymer. The rate of flow through the column can be controlled to allow completion of the desired reaction to occur by the time the α-hydroxyketone or ester is eluted.

When the enzyme is used for the synthesis of chiral esters of α-hydroxyketones, the enzyme, for example lipase PS-30, and an acylating agent, such as an acid anhydride, are used in the presence of a suitable solvent. The esterification can be carried out in an aprotic solvent, such as an ether, di-methylformamide (DMF), a nitrile (e.g. acetonitrile) or a hydrocarbon (such as hexane), by allowing the enzyme to affect acylation of the α-hydroxyketone in the presence of the acylating agent.

Scheme I illustrates the partial hydrolysis of an ester of an α-hydroxyketone, the acetate 4 or 8, according to the invention, to give a mixture of the resolved enantiomers, 4* or 8*, of the ester and the resolved enantiomers, 3* or 7*, of the α-hydroxyketone. Scheme I further illustrates the epimerization of the unreacted chiral ester to a racemic product (see the unbroken curved arrow), which can then be subjected to further resolution. Alternatively, if the resolved ester is desired, the resolved α-hydroxyketone can instead be acylated and racemized (see the broken curved arrow), and then subjected to further hydrolysis to provide more of the desired ester:

SCHEME I:

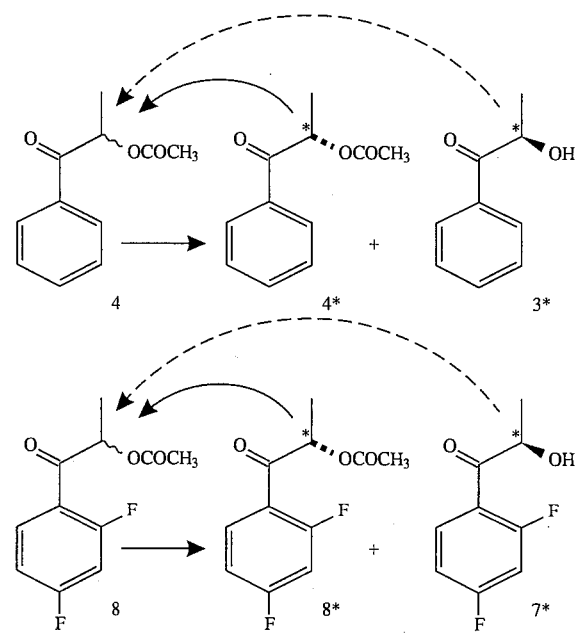

(An asterisk against a compound number indicates that that compound is enantiomerically enriched or pure.)

Esters of formula I, wherein $R^3$ is not H, can be used in the hydrolysis and in the epimerization. Epimerization of the unreacted ester can be carried out by treatment with base. Although organic bases are preferred, inorganic bases such as alkali metal hydroxides can be used. Preferred organic bases include lutidines, collidines, 4-dimethylaminopyridine (DMAP), 1,5-diazabicyclo[4,3,0]non-5-ene (DBN), 1,4-diazabicyclo[2,2,2]octane, (triethylenediamine, TED), 1,8-diazabicyclo[5,4,0]undec-7-ene (DBU), trialkylamines, such as triethylamine, and the commercially available base known as Dabco™ 33-LV.

Scheme II illustrates the partial acylation of an α-hydroxyketone, 3 or 7, according to the invention, to give a mixture of the resolved enantiomers, 9* or 10*, of the ester (in this case the hemisuccinate) and the resolved enantiomers, 3* or 7*, of the α-hydroxyketone. Scheme II further illustrates the epimerization of the unreacted chiral α-hydroxyketone to the racemic product (see the unbroken curved arrow), which can then be subjected to further resolution. Alternatively, if the resolved α-hydroxyketone is desired, the resolved ester can instead be hydrolyzed and racemized (see the broken curved arrow) and then subjected to further partial esterification to provide more of the desired α-hydroxyketone:

Hydroxyketones of the formula I, wherein $R^3$ is H, can be used in the esterification and in the epimerization.

SCHEME II:

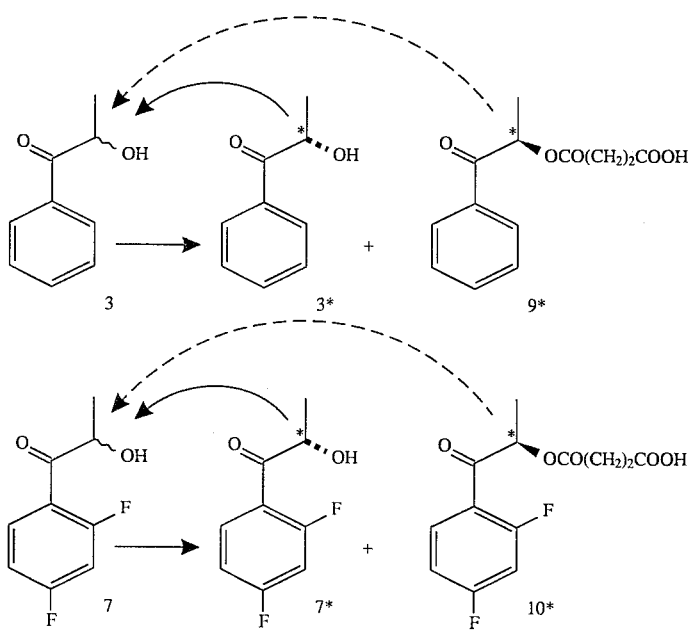

The necessary starting materials can be prepared by standard methods that are well-known to those skilled in the art. Some methods are indicated in Scheme III and the accompanying discussions, and are also illustrated in the Preparations immediately preceding the Examples.

SCHEME III

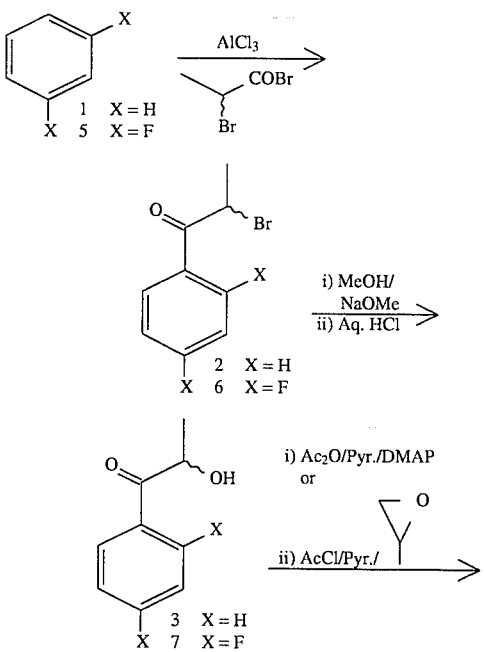

-continued
SCHEME III

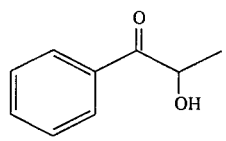

4  X = H
8  X = F

If desired, 2 and 6 can also be converted directly (e.g. with NaOAc, or with HOAc and base, such as $Et_3N$)into 4 and 8 respectively.

The following references illustrate the preparation of starting materials: (a) EPA No. 332,387; (b) U.S. Pat. No. 4,526,983; (c) EPA No. 178,533; (cl) Konosu et al., *Chem. Pharm. Bull.* 1990, 38, 2476; (e) De Kimpe et al., *Chem. Ber.*, 1983, 116, 3631.

The following Preparations and Examples are illustrative of the present invention. Numbers identifying the products correspond to the numbering of the compounds appearing in Schemes I, II and III.

PREPARATION 1

Step A: Add 45.5 mL (93.7 g, 0.43 mol) 2-bromopropionyl bromide in 15 mL CH$_2$Cl$_2$, dropwise, to a stirred mixture of 15.4 g (0.19 mol) benzene and 57.9 g (0.43 mol) AlCl$_3$ in 60 mL CH$_2$Cl$_2$ under N$_2$ at 0° C. Allow the stirred mixture to attain room temperature over 1 hour and then heat to 40° C. for 1.5 hours. Cool to room temperature and slowly pour the mixture over 300 g of vigorously stirred crushed ice. Treat the resulting suspension with 35 mL concentrated HCl and stir for 15 min. Separate the organic layer, wash successively with 2×100 mL saturated aqueous NaHCO$_3$, 2×100 mL water, and 2×10 mL saturated aqueous NaCl. Concentrate the organic layer to a residue. Dissolve the residue in 150 mL ether, then wash thoroughly with saturated aqueous NaHCO$_3$ until the aqueous phase remains basic. Separate the ether layer and wash with water, brine. Dry the ether layer over anhydrous Na$_2$SO$_4$ and concentrate in vacuo to yield 42.4 g (quantitative) of the product (2).

Step B: Add 8.5 g (0.157 mol) NaOMe in two equal portions, one hour apart, to a stirred solution of 20.2 g (0.09 mol) of the product of step A in 115 mL dry MeOH at 0° C., under N$_2$. Stir at 0° C. for 1 hour, then add 40 mL of cold (0° C.) 4N HCl. Stir for an additional 45 min. at 0° C. and then remove most of the methanol, under vacuum, while still cold. Extract the resulting suspension with 200 mL CH$_2$Cl$_2$. Wash the extract thoroughly with saturated aqueous NaHCO$_3$, then with brine, and dry over anhydrous Na$_2$SO$_4$. Concentrate in vacuo to yield 16.4 g (100% yield) of a residue. Chromatograph the residue (silica gel, CH$_2$Cl$_2$, then 3% ether in CH$_2$Cl$_2$ changing to ether) to obtain 9.9 g (70%) of the title compound (3).

PREPARATION 2

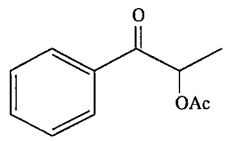

Method A: Add acetic anhydride (1.15 mL, 12.19 mmol) and then a catalytic amount of DMAP to a stirred solution of 1.53 g (10.2 mmol) of the product of Preparation 1 in 10 mL CH$_2$Cl$_2$, under N$_2$ at 0° C. Warm the mixture to room temperature and stir for 4 hr. Dilute with 15 mL CH$_2$Cl$_2$, then wash successively with saturated aqueous Na$_2$CO$_3$, water, and saturated aqueous NaCl. Dry over anhydrous MgSO$_4$, then concentrate in vacuo to a residue. Flash chromatography of the residue (silica gel; 5% ether in CH$_2$Cl$_2$, then 10% ether in CH$_2$Cl$_2$,) gave 1.66 g (85%) of the title compound (4).

Method B: Add pyridine (0.138 mL, 1.60 mmol) to a stirred solution of 0.20 g ((1.33 mmol) of the product of Preparation 1 in 2 mL CH$_2$Cl$_2$ at 0° C., under N$_2$. Slowly add 0.115 mL (1.60 mmol) acetyl chloride, then allow the mixture to attain room temperature and stir for 1.5 hours. Remove the volatiles under vacuum and dissolve the residue in 30 mL ether. Wash with 5 mL water, 10 mL saturated aqueous NaHCO$_3$ (the aqueous phase remained basic), and 10 mL saturated aqueous NaCl, then dry over anhydrous Na$_2$SO$_4$+MgSO$_4$. Concentrate in vacuo to a residue, then chromatograph (silica, 7:1 CH$_2$Cl$_2$:ether) to give 0.24 g (92%) of the title compound (4).

Method C: Add 0.017 mL of pyridine, and then 0.29 mL (4.10 mmol) propylene oxide and 0.64 mL (9.03 mmol) acetyl chloride to a stirred solution of 0.308 g (2.05 mmol) of the product of Preparation 1 in 3 mL dry CH$_2$Cl$_2$, under N$_2$. Heat at reflux for 5 hours, then add 0.16 mL (2.1 mmol) acetyl chloride. Heat at reflux overnight, then remove the volatiles under vacuum. Dissolve the resulting residue in 30 mL ether, then wash with saturated aqueous NaHCO$_3$, water, and saturated aqueous NaCl. Dry over anhydrous Na$_2$SO$_4$+MgSO$_4$, then concentrate to a residue. Chromatograph the residue (silica gel, 6:1 CH$_2$Cl$_2$:ether) to give 0.30 g (76%) of the title compound (4).

Anal: C$_{11}$H$_{12}$O$_3$: Theory: C, 68.8; H, 6.3. Found: C, 68.4; H, 6.4.

PREPARATION 3

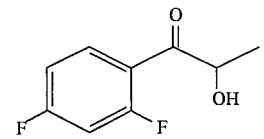

Step A: Add 122 mL (1.16 mol) 2-bromopropionyl bromide, dropwise, over 1 hour to a stirred mixture of 52 mL (60 g, 0.52 mol) 1,3-difluorobenzene (5), 155 g (1.16 mol) AlCl$_3$ and 100 mL CH$_2$Cl$_2$ under N$_2$, while maintaining the mixture at room temperature. Stir at room temperature for 2 hours and then heat to 35°–40° for 1.5 hours. Slowly cool to about 10° C., then slowly pour into 900 g of vigorously stirred crushed ice. Separate the organic layer and extract the aqueous layer with 500 mL ether. Keep the CH$_2$Cl$_2$ and ether layers separate. Wash the CH$_2$Cl$_2$ layer with saturated aqueous Na$_2$CO$_3$ solution until the aqueous layer remains alkaline, then concentrate in vacuo to a residue. Add the residue to the ether layer obtained above. Wash the ether solution with saturated aqueous Na$_2$CO$_3$ solution until the aqueous layer remains basic, then washed with water, followed by saturated NaCl solution. Concentrate in vacuo to yield 130 g (100%) of the product (6)

Step B: Add two 43.8 g (0.81 mol) portions of NaOMe, 1 hour apart, to a stirred solution of 100.9 g (0.39 mol) of the product of Step A in 800 mL dry MeOH at 0° C., under N$_2$. Stir for 1 hour, then add 500 mL of cold (0° C.) 4N HCl. Stirred at 0° C. for 1 hour, then remove most of the MeOH, under vacuum, while still cold. Extract with 500 mL CH$_2$Cl$_2$, then wash with 2×400 mL saturated aqueous NaHCO$_3$ (the aqueous wash remained alkaline after the second wash), 400 mL H$_2$O, 400 mL saturated aqueous NaCl. Dry over anhydrous MgSO$_4$, then concentrate in vacuo to yield 70.6 g (97.3%) of a residue. Recrystallize from petroleum ether to yield 59.0 g (82.3%) of the title compound (7), mp. 49°–51°.

PREPARATION 4

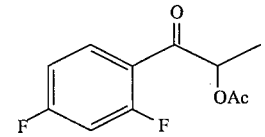

Method A: Add 0.61 mL (6.46 mmol) acetic anhydride and then a catalytic amount of DMAP to a stirred solution of 1.0 g (5.37 mmol) of product of Preparation 3 in 10 mL CH$_2$Cl$_2$ at 0° C. under N$_2$. Allow the mixture to attain room temperature and stir overnight. Dilute with 10 mL CH$_2$Cl$_2$ and work up as described in Preparation 2, Method A, to give 1.13 g (92.2%) of the title compound (8).

Method B: Slowly add 0.277 mL (3.22 mmol) pyridine and then 0.23 mL acetyl chloride (3.22 mmol) to a stirred solution of 0.5 g (2.68 mmol) of the product of Preparation 3 in 4 mL $CH_2Cl_2$ at 0° C., under $N_2$. Allow the mixture was allowed to reach room temperature, stir for 1.5 hours, then concentrate to a residue. Dissolve the residue in 25 mL ether, wash with 10 mL water, 15 mL saturated aqueous $NaHCO_3$, and 15 mL saturated aqueous NaCl, then dry over $Na_2SO_4+MgSO_4$. Concentrate in vacuo to yield 0.62 (quantitative) of the title compound (8).

Method C: Add 0.46 mL (6.44 mmol) acetyl chloride, 0.45 mL (6.44 mmol) propylene oxide, and a catalytic amount of DMAP to a stirred solution of 1.0 g (5.37 mmol) of the product of Preparation 3 in 10 mL $CH_2Cl_2$ at 0° C. under $N_2$. Allow the mixture to attain room temperature and stir for 3 hours. Add 0.38 mL acetyl chloride and heat at 37°–40° C. for 3 hours. Add 0.45 mL propylene oxide and continue heating for 8 hours. The reaction is driven to completion by adding 0.52 mL pyridine. Cool the mixture to room temperature and concentrate to a residue under vacuum. Add 25 mL ether, wash with saturated aqueous $NaHCO_3$ (the aqueous layer remained basic), water, and saturated aqueous NaCl, then dry over anhydrous $MgSO_4$. Concentrate in vacuo, then chromatograph (silica gel, 7:1 $CH_2Cl_2$:ether) to yield 0.95 g (77.5%) of the title compound (8).

Anal: $C_{11}H_{10}O_3F_2$: Theory: C, 57.9; H, 4.4; F, 16.7. Found: C, 57.5; H, 4.3; F, 16.6.

EXAMPLES

Chiral α-Hydroxy-propiophenones by Enzymatic Hydrolysis of Esters:

The following present typical procedures that were used to obtain chiral α-hydroxyketones 2 and 6 listed in the Table below. The enantiomeric ratios of the esters and of the hydroxyketones can be determined by using Chiracel® AS and Chiracel® OB HPLC columns, respectively, with 7% 2-propanol in hexane as the mobile phase.

EXAMPLE 1

Hydrolysis With LPL (Lipoprotein Lipase) Enzymes: e.g. Hydrolysis of Acetate 8:

Add 0.040 g of the enzyme LPL-200 to a stirred suspension of 1 g of racemic 8 in 10 mL of a 0.2 M phosphate buffer (pH=7). Stir the mixture at room temperature for 11 h., then extract by sonication with 2×100 mL of 7% 2-PrOH in hexanes, followed by 50 mL of hexanes. Concentrate the combined extracts and separate the chiral products by flash column chromatography (silica gel, 7:1 $CH_2Cl_2$:ether) to yield 0.35 g (48%) of chiral 7 with R:S ratio of 99.5:0.5, $[\alpha]_D=+73.3°$ (c=1, $CHCl_3$); and 0.51 g (51%) of chiral 8 with R:S ratio of 2.6:97.4, $[\alpha]_D=-35.4°$,(c=1, $CHCl_3$).

EXAMPLE 2

Hydrolysis of Acetate 4 with PS-30 enzymes (from Pseudomonas):

Add lipase AK (0.3 g) to a stirred suspension of 1.1 g racemic 4 in 10 mL of a 0.2 M phosphate buffer (pH=7). Stir the mixture at room temperature for 72 h., then extract and separate the chiral compounds, as described in Example 1, to yield 0.35 g (40%) of chiral 3 with R:S ratio of 99:1, $[\alpha]_D=+85.1°$ (c=1, $CHCl_3$); and 0.66 g (60%) of chiral 4 with R:S ratio of 6:94, $[\alpha]_D=-37.8°$ (c=1, $CHCl_3$).

EXAMPLE 3

This Example gives further results obtained by enzymatic hydrolysis of hydroxyesters. The Control (Experiment No. 1) is obtained in dilute solution containing approximately 60 μg ester substrate in 2 mL of a 0.2 M phosphate buffer (pH=7), with 7 to 20 mg of enzyme. Screening experiments (to discover whether or not an enzyme is active and in particular would yield a chiral product) are also carried out in dilute solution. When it is found that an enzyme has potential utility in the process of the present invention, a further experiment is then carried out using a more concentrated solution of the α-hydroxyester, e.g. as in Example 2. The results of such experiments are tabulated in the following Table. An experiment is considered to show "useful results" when the hydrolysis proceeds to at least 50% completion in 96 hours and the product is obtained in an enantiomeric excess (e.e.) of at least 45%:

TABLE

Enzymatic Hydrolysis of Racemic Acetate 8.

| Expt No. | Enzyme | Source | % hydrolyzed product/time | R/S Ratio of 7, R:S (ee) |
|---|---|---|---|---|
| 1 | NONE (Control) | — | 17%/96 hours | ~50:50 |
| 2 | Lipase | Hog pancreas | 17%/48 hours, 25%/96 hours | 89:11 (78) |
| 3 | Lipase Type XIII | Pseudomonas sp. | 100%/4 hours | 53:46 (7) |
| 4 | Lipase Type II | Porcine pancreas | 25%/24 hours, 28%/96 hours | 87:13 (74) |
| 5 | Esterase Type I | Porcine liver | 57%/2 hours | 85:15 (70) |
| 6 | Lipase AK | Pseudomonas sp. | 46%/72 hours | 95:5 (90) |
| 7 | Lipase PS-30 | *Pseudomonas cepacia* | 47%/72 hours | 95:5 (90) |
| 8 | Lipase CES | Pseudomonas sp. | 60%/96 hours | 87:13 (74) |
| 9 | Lipase AP-6 | *Aspergillus niger* | 51%/96 hours | 27:73 (46) |
| 10 | Lipase AP-12 | *Aspergillus niger* | 50%/28 hours | 18:82 (64) |
| 11 | β-Glucuronidase | Bovine liver | 49%/22 hours | 91:9 (82) |
| 12 | Enterokinase | Bovine intestine | 47%/96 hours | 75:25 (50) |
| 13 | Urease Type X | *Bacillus pasteurii* | 56%/96 hours | 93:7 (86) |
| 14 | PLE-A-Amano | Porcine liver | 45%/4 hours | 87:13 (74) |
| 15 | LPL-50S | Amano (Pseudomonas sp.) | 54%/5 hours | 96:4 (92) |
| 16 | LPL-80 | Amano (Pseudomonas sp. | 53%/5 hours | 97:3 (94) |
| 17 | LPL-200S | Amano (Pseudomonas sp.) | 52%/3 hours | 99:1 (98) |

The following enzymes did not to show "useful results", using the substrates tested herein:

Lipases: Lipase AY-30, Lipase Type VII and Lipase Type VII-S from *Candida cylindracea;* Lipase L-10 from *Candida lipolytica;* Lipase MAP-10 from *Mucor javanicus;* Lipase G from Penicillium sp.; Lipase R-10 from *Penicillum roqueforti;* Lipase GC-20 from *Geotricum candidum;* Lipase CE from *Humicola langinosa;* Lipase N from *Rhisopus niveus;* Lipase D from *Rhizopus delemer,* Lipase (I) from wheat germ; Lipase PGE from calf (tongue and salivary glands); Lipase F Amano-15;

Proteases: Protease Type XXIV from bacteria; Protease Type XVI from *Bacillus subtilis;* Protease Type K from *Bacillus thermoproteolyticus*; Protease Type IX from *Bacil-* lus polymyxa; Protease Type XXIII from *Aspergillus orgaze;* Protease Type XIII and Protease Type XIII from *Aspergillus saitoi;* Protease Type XIV and Protease Type XXI from *Streptomyces griseus;* Protease Type XVIII from *Rhizopus* sp.; Protease Type XXVII; Protease Type XXIV; Protease Type IV from *Streptomyces caespitosus;*

β-Glucuronidases: β-Glucuronidase from *Helix pomatia,* from Scallops (*Chlamys opercularis*), from bovine liver and from bovine pancreas;

Other enzymes: Trypsin and δ-Chymotrypsin from bovine pancreas; Cholinesterase Acetyl Type XII-S from bovine erythrocytes; 'Prozyme 6'.

However, some of these might be appropriate with particular substrates.

EXAMPLE 4

The following Table shows further results obtained by enzymatic hydrolysis of α-hydroxy esters:

TABLE

Enzymatic Hydrolysis of Racemic Acetate 4.

| Expt No. | Enzyme | Source | % hydrolyzed product/time | R/S Ratio of 7, R:S (ee) |
|---|---|---|---|---|
| 1 | Lipase AK | Pseudomonas sp. | 45%/75 hours | 99:1 (98) |
| 2 | Lipase PS-30 | Pseudomonas cepacia | 48%/75 hours | 92:8 (84) |

EXAMPLE 5

Racemization of Esters of Chiral α-Hydroxyketones:

1. Epimerization of Chiral 4: Add 0.010 mL of DBN to a solution of 0.15 g of 4 (R:S ratio of 10:90) in 1.5 mL THF at room temperature and stir for 24 h. Filter through a silica gel plug (ether) to yield 0.125 g (83% mass balance) of an oil. HPLC and NMR analysis of this oil indicates that 85% of this mass is racemic 4 with R:S ratio of ≈45:55, suitable for enzymatic generation of (R)-3 as described above.

2. Epimerization of Chiral 8: Racemization of chiral 8 (R:S ratio of 15:85), 0.22 g, with DBN, as described above, yields 0.22 g of an oil consisting of 66% of racemic 8 with R:S ratio of 46:54. This oil is suitable for enzymatic generation of (R)-7 as described above.

Where impurities hinder the racemization, additional base and/or longer reaction times may be necessary.

Example 6

Enzymatic Esterification of Racemic α-Hydroxyketones;
Enzymatic Isolation of Chiral α-Hydroxyketones in Organic Solvents, and Synthesis of their Esters:
This Example shows that the aqueous phase can often be dispensed with altogether.
Isolation of Chiral 3 and Synthesis of Chiral 9:

Add 0.067 g (0.67 mmol) succinic anhydride and then 0.035 g of Lipase PS-30 to a stirred solution of 0.10 g (0.67 mmol) 3 in 5 mL of ether (which had not been dried) at room temperature under $N_2$. The mixture is stirred for 96 hours, then diluted with 10 mL ether, sonicated for a few minutes and filtered. The filtration residue is washed with 10 mL hexane and the combined organic solutions washed with 2×10 mL by 2×10 mL of 0.2 M phosphate buffer (pH=7), then concentrated in vacuo to yield 0.039 g (39%) of chiral 3 with an R:S ratio of 31:69 as determined by chiral HPLC.
Isolation of Chiral 7 and Synthesis of Chiral 9:

Add 0.54 g (0.54 mmol) succinic anhydride and then 0.035 g Lipase PS-30 to a stirred solution of 0.10 g (0.54 mmol) 7 in 5 mL ether. After treatment as described above, 0.060 g (65%) of chiral 7 with an R:S ratio of 33:67 was obtained.

The descriptions of the foregoing embodiments of the invention have been presented for purpose of illustrative and not intended to limit the scope of this invention to the precise forms disclosed. Many modifications and variations are possible in light of the above teaching. The exemplified embodiments serve to illustrate the principles of the invention clearly and thereby enable others skilled in the art to utilize the invention in the best mode possible and in various embodiments and with various modifications such as are suited to the particular use contemplated. The scope of the invention is defined only by the claims appended hereto.

I claim:

1. A process for the preparation of a chiral α-hydroxyketone of the formula

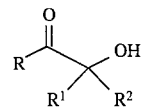

wherein:
R is selected from the group consisting of phenyl and substituted phenyl; and
$R^1$ is hydrogen and $R^2$ is alkyl;
which comprises:
selectively hydrolyzing an ester of a racemic α-hydroxyketone having the formula

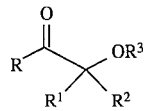

wherein $R^3$ is a carboxylic acyl group of the formula $R^4$—C(O)— and $R^4$ is alkyl or substituted alkyl, with an enzyme that has a specificity for one enantiomer, wherein the enzyme is selected from the group consisting of porcine pancreatic lipase, Lipase from Pseudomonas, Lipase from *Aspergillus niger*, Lipase Type II from porcine pancreas, Esterase Type I from Porcine liver, β-Glucuronidase from Bovine liver, Enterokinase from Bovine intestine, Urease Type from *Bacillus pasteurii*, and Ple-A from Porcine liver;
and isolating said chiral α-hydroxyketone.

2. The process of claim 1 wherein $R^4$—C(O)— is acetyl, propionyl, butyryl, malonyl, oxalyl, gluconyl, succinoyl or chloroacetyl.

3. The process of claim 2 wherein the hydrolysis is carried out in:
aqueous solution; or
a mixture of an aqueous solution and a water-miscible organic solvent; or
an aqueous solution in the presence of a water-immiscible organic solvent and either a solubilizing agent that improves the miscibility of the phases or a chemical that encourages phase transfer of the α-hydroxy ketone ester, product or enzyme.

4. The process of claim 3 wherein the organic solvent is methanol, ethanol, 2-propanol, acetone, dimethoxyethane, or dimethysulfoxide.

5. The process of claim 1 wherein the enzyme is supported on a polymer.

6. The process of claim 1 further comprising racemizing unchanged enantiomers and recycling the resulting racemate through the selective hydrolysis, as described above.

7. The process of claim 1 wherein the Lipase from Pseudomonas is selected from the group consisting of Lipase Type XIII, Lipase AK, Lipase PS-30, Lipase CES, LPL-50S, LPL-80 and LPL-200S.

8. A process for the preparation of an ester of a chiral α-hydroxyketone of the formula

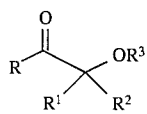

wherein:

R is selected from the group consisting of phenyl and substituted phenyl;

$R^1$ is hydrogen and $R^2$ is alkyl;

$R^3$ is a carboxylic acyl group of the formula $R^4$—C(O)—;

$R^4$ is alkyl or substituted alkyl;

which comprises:

selectively esterifying a racemic α-hydroxyketone of the formula

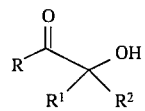

wherein R, $R^1$ and $R^2$ are as defined above, with an esterifying agent in the presence of an enzyme that favors the preparation of one enantiomer, wherein the enzyme is selected from the group consisting of porcine pancreatic lipase, Lipase from Pseudomonas, Lipase from *Aspergillus niger*, Lipase Type II from porcine pancreas, Esterase Type 1 from Porcine liver, β-Glucuronidase from Bovine liver, Enterokinase from Bovine intestine, Urease Type X from *Bacillus pasteurii,* and PLE-A from Porcine liver;

and isolating said chiral ester thereof.

9. The process of claim 8 wherein $R^4$—C(O)— is acetyl, propionyl, butyryl, malonyl, oxalyl, gluconyl, succinoyl or chloroacetyl.

10. The process of claim 8 further comprising racemizing unchanged enantiomers and recycling the resulting racemate through the selective esterification as described above.

11. The process of claim 8 wherein the α-hydroxyketone is esterified in an aprotic solvent.

12. The process of claim 8 wherein the Lipase from Pseudomonas is selected from the group consisting of Lipase Type XIII, Lipase AK, Lipase PS-30, Lipase CES, LPL-50S, LPL-80 and LPL-200S.

* * * * *

UNITED STATES PATENT AND TRADEMARK OFFICE
CERTIFICATE OF CORRECTION

PATENT NO. : 5,545,558

DATED : August 13 1996

INVENTOR(S) : Dinesh Gala

It is certified that error appears in the above-identified patent and that said Letters Patent is hereby corrected as shown below:

Column 14 line 46: Insert --X-- after "Type";

Column 14 line 47: Cancel "Ple-A" and insert --PLE-A--.

Signed and Sealed this

Twelfth Day of November, 1996

Attest:

BRUCE LEHMAN

Attesting Officer

Commissioner of Patents and Trademarks